United States Patent [19]

Hechtman

[11] Patent Number: 5,595,753
[45] Date of Patent: Jan. 21, 1997

[54] TOPICAL FORMULATIONS AND METHODS FOR TREATING HEMORRHOIDAL PAIN AND SPHINCTER AND SMOOTH MUSCLE SPASM IN THE GASTROINTESTINAL TRACT

[75] Inventor: Herbert B. Hechtman, Chestnut Hill, Mass.

[73] Assignee: President and Fellows of Harvard College, Cambridge, Mass.

[21] Appl. No.: 422,350

[22] Filed: Apr. 14, 1995

[51] Int. Cl.$^6$ .............................. A61F 9/02; A61K 9/68; A01N 37/12; A01N 37/18
[52] U.S. Cl. .................. 424/436; 424/434; 424/440; 514/551; 514/565; 514/616; 514/621
[58] Field of Search ...................... 514/551, 565, 514/616, 621; 424/434, 436, 440

[56] References Cited

U.S. PATENT DOCUMENTS

| | | | |
|---|---|---|---|
| 4,663,289 | 5/1987 | Veech | 435/240 |
| 5,217,997 | 6/1993 | Levere et al. | 514/565 |
| 5,246,704 | 9/1993 | Sakaguchi et al. | 424/433 |
| 5,428,070 | 6/1995 | Cooke et al. | 514/557 |

OTHER PUBLICATIONS

Loeb S. A., "Hemorrhoidectomy: Method for Elimination of Post–Operative Pain Due to Sphincter Spasm," Am. J. Proctol. 25(6):37–42 (1974).
Miller et al., "Dicyclomine for medical management of persistent anal fissure with associated spasm of the inernal sphincter," Tex. Med. 88(11):65–66 (1992).
Jostarndt et al., "Functional Pathomechanisms of Anal Fissure," Langenbecks Arch. Chir. 368(2):97–103 (1986).
Vanderwinden et al., "Nitric Oxide Synthase Activity In Infantile Hypertrophic Pyloric Stenosis," New England Journal of Medicine 327 (8):511–515 (1992).
Pickering et al., "Prevention of Smooth Muscle Cell Outgrowth from Human Atherosclerotic Plaque by a Recombinanant Cytotoxin Specific for the Epidermal Growth Factor Receptor," J. of Clin. Invest. 91:724–729 (1993).
Rattan et al., "Role of nitric oxide as a mediator of internal anal sphincter relaxation," Amer. Phys. Soc. pp. G107–G112 (1992).
Rattan et al., "Inhibitory effect of CO on internal anal sphincter: heme oxygenase inhibitor inhibits NANC relaxation," Amer. Phys. Soc. pp. G799–G804 (1993).
Bayguinov et al., "Role of nitric oxide as an inhibitory neurotransmitter in the canine pyloric sphincter," Amer. Phys. Soc. pp. G975–G983 (1993).
Chakder et al., "Release of nitric oxide by activation of nonadrenergic noncholinergic neurons of internal anal sphincter," Amer. Phys. Soc. pp. G7–G12 (1993).
Conklin et al., "Characterization and Mediation of Inhibitory Junction Potentials From Opossum Lower Esophageal Sphincter," Gastroenterology 104:1439–1444 (1993).
Tottrup et al., "Involvement fo the L–Arginine–Nitric Oxide Pathway in Internal Anal Sphincter Relaxation," Gastroenterology 102:409–415 (1992).

(List continued on next page.)

Primary Examiner—Carlos Azpuru
Attorney, Agent, or Firm—Weingarten, Schurgin, Gagnebin & Hayes LLP

[57] ABSTRACT

A topical treatment for hemorrhoidal pain and for spasms of the sphincters and muscles located in the gastrointestinal (GI) tract is disclosed. The topical preparation includes the amino acid L-arginine in a pharmaceutically acceptable carrier substance, e.g., K-Y jelly, suppository, or ingestible formulation, and can be applied directly to the affected area. The topical preparation of the invention is effective for relieving the pain of hemorrhoids or for treating conditions resulting from spasms of sphincters of the GI tract including anal fissure, post operative rectal pain, hypertrophic pyloric stenosis, and pancreatitis, as well as conditions resulting from general spasm of the muscles of the GI tract.

29 Claims, 2 Drawing Sheets

OTHER PUBLICATIONS

Rattan et al., "Nitric Oxide Pathway in Rectoanal Inhibitory Reflex of Opossum Internal Anal Sphincter," 103:43–50 (1992).

Kiechle et al., "Nitric Oxide," Clin. Chem. 100(5):567–575 (1993).

Morris et al., "New insights into the regulation of inducible nitric oxide synthesis," Amer. Phys. Soc. pp. E829–E839 (1994).

Totturp et al., "Nitric oxide mediating NANC inhibition in oppossum lower esophageal sphincter," Amer. Phys. Soc. pp. G385–G389 (1991).

Tottrup et al., "The role of the L-arginine–nitric oxide pathway in relaxation of the opossum lower oesophageal sphincter," J. Pharmacol. 104:113–116 (1991).

De Man et al., "The role of nitric oxide in inhibitory non–adrenergic non–cholinergic neurotransmission in the canine lower oesophageal sphincter," pp. 1093–1096.

Pauletzki et al., "Involvement of L-arginine–nitric oxide pathways in neural relaxation of the sphincter of Oddi," Eur. Journ. of Pharm. 232:263–270 (1993).

Anderson et al., "Characterization of the adenosine receptors mediating hypothermia in the conscious mouse," pp. 1386–1390.

TOPICAL FORMULATIONS AND METHODS FOR TREATING HEMORRHOIDAL PAIN AND SPHINCTER AND SMOOTH MUSCLE SPASM IN THE GASTROINTESTINAL TRACT

FIELD OF THE INVENTION

This invention relates to control of hemorrhoidal pain and spasms of the sphincters and muscles in the gastrointestinal tract.

BACKGROUND OF THE INVENTION

Sphincters are circular groups of smooth muscle that control the orifices of hollow organs. Sphincters present throughout the gastrointestinal (GI) tract control the passage of materials through this system of the body. When constricted, the sphincters close orifices leading to the hollow organs, such as the stomach, intestine, anus, etc. In order for the sphincter to open, the muscles must relax.

The sphincter that closes the anus (sphincter ani) consists of two sphincter muscle groups. The external anal sphincter is a thin flat plane of striated muscle fibers adherent to the integument surrounding the margin of the anus. The internal anal sphincter (IAS) is a ring of smooth muscle which surrounds the lower extremity of the rectum and is formed by an aggregation of the involuntary circular fibers of the intestine. Inflammation locally may cause sphincter spasm and pain. Thus, dilation of the veins in the anorectal area results in the condition known as hemorrhoids. Frequently, the hemorrhoidal condition is accompanied by bleeding, thrombosis, inflammation, and pain around the area of the rectum. The pain associated with hemorrhoids is due primarily to the inflammation adjacent to the anal sphincter.

Anal sphincter spasm is a condition in which the muscles of the internal anal sphincter are under abnormal tension. The strong contractions of the internal anal sphincter associated with sphincter spasm often give rise to painful linear ulcers or crack-like sores, known as rectal fissures, on the margin of the anus. Anal sphincter spasm is also considered a cause of the pain following rectal surgery or thrombosed hemorrhoids.

Current treatments of rectal fissures are directed at relieving sphincter spasm and include dilatation (under anesthesia) or cutting a part of the sphincter (lateral internal sphincterotomy). Applications of heat, cold, witch hazel, topical anesthetics, topical steroids, stool softeners, and bed rest have also been prescribed to treat rectal pain. However, none of these approaches significantly modifies the sphincter spasm itself.

A known moderator of sphincter tone is nitric oxide (NO). Nitric oxide has been shown to bring about a concentration-dependent reduction in the resting tension of internal sphincter smooth muscle strips in vitro (Rattan et al., Am. J. Physiol. 262:G107–112 (1992)). It has also been shown that L-arginine acts as a competitive inhibitor of compounds that block the action of NO production. NO has also been shown to mediate adaptive relaxation of other sphincters in the gastrointestinal tract including the lower esophageal sphincter (Conklin et al., Gastroenterology 104:1439–1444 (1993); Tottrup et al., Br. J. Pharmacol. 104:113–116 (1991)), pyloric sphincter (Bayguinov et al., Am. J. Physiol. 264:G975–983 (1993), sphincter of Oddi (Mourelle et al., Gastroenterology 105:1299–1305 (1993)), and the ileocolic sphincter (Ward et al., Br. J. Pharmacol. 105:776–782 (1992)). It is thought that NO or NO-like substances serve as important control mechanisms for the general phenomenon of gastrointestinal adaptive relaxation.

Currently there is no safe, effective, topical treatment available to treat patients suffering from spasms of sphincters located in the GI tract. Direct administration of NO gas is not a desirable method to induce sphincter relaxation because NO binds to hemoglobin and reduces oxygen transport to tissues throughout the body. In addition, NO is an unstable compound and has a short half life. High doses of NO gas would therefore be required; however, high doses of NO are cytotoxic.

Topical preparations of glycerol trinitrate have been examined as mediators of anal sphincter tone (Loder et al., Br. J. Surgery 81:1386–1389 (1994)). However side effects, such as headaches, were observed in the test patients. Esophageal spasm has also been treated with systemic application of nitroglycerin and long-lasting nitrates (Swamy et al., Gastroenterology 72:23–27 (1977)). However, the systemic use of these smooth muscle dilators may yield unwanted vascular effects.

SUMMARY OF THE INVENTION

The invention features topical treatment for hemorrhoidal pain and for spasms of the mammalian, especially the human, gastrointestinal (GI) tract using a topical preparation including the amino acid L-arginine in a pharmaceutically acceptable carrier substance, e.g., K-Y jelly, suppository, or ingestible solution. In one embodiment, the concentration of L-arginine is in the range of approximately 0.01 to 10 mg per 0.1 ml carrier. The topical preparation of L-arginine is applied directly to the affected area. Depending on the concentration of the L-arginine in the carrier, application of the topical preparation relieves hemorrhoidal pain and relaxes sphincter tension in approximately 10 minutes.

The invention generally features a topical treatment for a medical condition of the gastrointestinal tract, e.g., hemorrhoidal pain and for spasms of the sphincters and smooth muscles of the human gastrointestinal tract. As used herein, the term "gastrointestinal tract" is defined as the part of the body which includes the esophagus, stomach and small and large intestines. The terms "topical" and "topical application" are defined as application to the mucosal surfaces of the body and include applications to areas of the gastrointestinal tract. The term "spasm" is defined herein to include any strong involuntary movement or muscular contraction lasting for a prolonged period. The term "anorectal area" is defined herein to includes both the anus and the rectum.

The topical preparation of the invention is effective for treating a medical condition such as hemorrhoidal pain and for treating spasms of the sphincters or other muscles located in the human GI tract including the internal anal sphincter, lower esophageal sphincter, pyloric sphincter, sphincter of Oddi, and the ileocolic sphincter. The topical preparation is also useful in treating conditions resulting from spasms of sphincters of the GI tract including anal fissure, post-operative rectal pain, hypertrophic pyloric stenosis, and pancreatitis, as well as conditions resulting from general spasm of the muscles of the GI tract including Zenkers diverticulum, achalasia, esophageal spasm (nutcracker esophagus), irritable bowel disease, and Hirshprungs disease (bowel obstruction). As used herein, "effective amount" refers to an amount of the L-Arginine-containing topical preparation, in the dosages disclosed herein, that results in treatment of the medical condition, i.e., reduction in pain or muscle spasm. Reduction in pain is subjectively determined by the user, and will include any perceptive lessening of pain. Alternatively, an "effective amount" may be determined by monitoring reduction in sphincter spasm, as disclosed herein.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1:
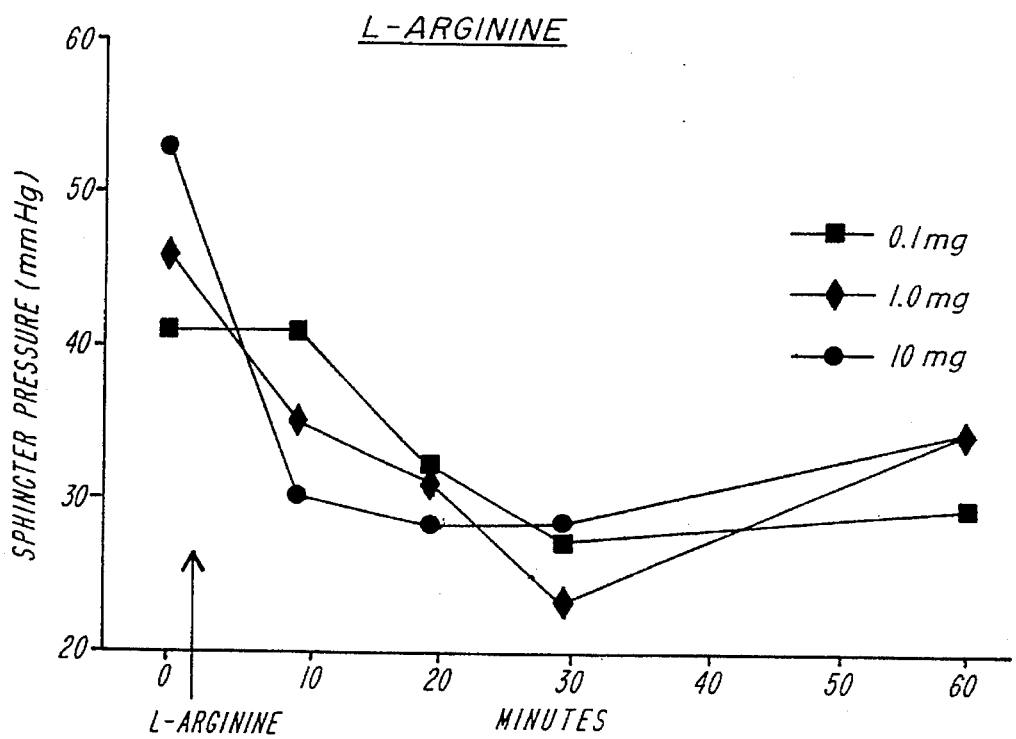
FIG. 1 is a graph of sphincter pressure as a function of time after L-arginine is applied.

L-arginine in a preselected dosage is prepared for local topical application by mixing in a suitable carrier vehicle such as K-Y jelly, suppository, and the like. Preferably, the concentration of L-arginine is in the range of approximately 0.0001 to 10 mg per 0.1 ml of carrier, and more preferably in the range of approximately 0.01 to 10 mg per 0.1 ml carrier.

Carrier for the topical application can be any inert substance, such as a water soluble (e.g., K-Y) jelly, suppository, enema solution, saline solution, dimethylsulfoxide (DMSO), and the like, or incorporated in a dissolvable sucker or ingestible formula for application by mouth. Choice of carrier depends on several factors including the intended application and degree of the particular spasm. In one embodiment, L-arginine is mixed with K-Y jelly or added to a suppository for treatment of hemorrhoidal pain or spasm of the internal anal sphincter. In general, carriers with higher densities, such as K-Y jelly or suppositories, are capable of providing an area with a prolonged exposure to the active ingredients. A solution formulation, such as an enema solution or DMSO, on the other hand, provides immediate exposure of the active ingredient to the chosen area, however, the effects do not last as long. Implementation of a dissolvable sucker permits exposure of the muscles of the esophagus and upper GI tract to the treatment by swallowing as the sucker dissolves.

At least two types of NO synthase enzymes contribute to production of NO. An inducible NO synthase depends upon protein synthesis of the enzyme before NO production begins. A constitutive NO synthase enzyme is present in endothelial cells, platlets, brain, and smooth muscle cells. It is likely that L-arginine directly activates the constitutively expressed NO synthase enzyme to cause production of NO or a related compound, since sphincter relaxation occurs within ten minutes of application of this agonist. Following NO production, guanylate cyclase is activated in smooth muscle which leads to the formation of cyclic guanosine 3',5'-monophosphate (cGMP), a transduction mechanism for a number of stimuli in addition to those leading to muscle relaxation and vasodilatation.

The following examples are presented to illustrate the advantages of the present invention and to assist one of ordinary skill in making and using the same. These examples are not intended in any way to otherwise limit the scope of the disclosure.

EXAMPLE I

Testing and Monitoring of Effect of L-Arginine on Sphincter Pressure

A topical preparation according to the invention is tested on sphincter muscle as follows.

Male Sprague-Dawley rats (475–525 g) are permitted a 3 hour stabilization period in the laboratory prior to the start of the experiment. The unanesthetized rats are placed in a plastic restraint (Poly Film Restraint Cone, Cervical Dislocators, Inc. Wausau, Wis.) for containment during rectal sphincter pressure monitoring. A 13 Fr pediatric anorectal motility catheter equipped with an extra small latex balloon with dimensions of 4 mm diameter and 21 mm length, the approximate size of a rat dropping (Synectics Medical Inc., Irving, Calif.) is introduced into the rectum and inflated with 1 ml water. The rat is allowed to acclimatize for 1 minute before recording rectal pressure. If stool is present in the rectum, it may be evacuated using a gentle external milking action. Pressure is measured with a transducer (Model 800, Bentley Tanstec Inc., Irvine, Calif.). Approximately 30 to 40 mm Hg rise in pressure occurs as a result of balloon inflation and the reflex spasm. A stable baseline returns after approximately 1 minute. If the rectal spasm is not reversed within 2 minutes, the animal is not used. Between periods of rectal pressure monitoring animals are placed in containment cages. Pressures are assayed at 10, 20, 30 and 60 minutes. Additional readings can be taken at 90 minutes.

Sphincter pressure in control animals treated with saline is stable providing that noise, motion or rough handling are avoided. After recording baseline pressure, saline carrier or L-arginine (Sigma Chemical Co., St. Louis, Mo.) in doses of 0.01 to 10 mg per 0.1 ml saline carrier is introduced into the rectal lumen with a tuberculin syringe. As shown in FIG. 1 and Table 1, animals treated with L-arginine in dosages of 0.01 to 10 mg/0.1 ml show a decline in rectal pressure. The earliest decrease occurs at 10 minutes and the effect is still apparent after 1 hour. No effect is noted with L-arginine at a dose of 0.0001 mg/0.1 ml (Table 1).

Figure 2:
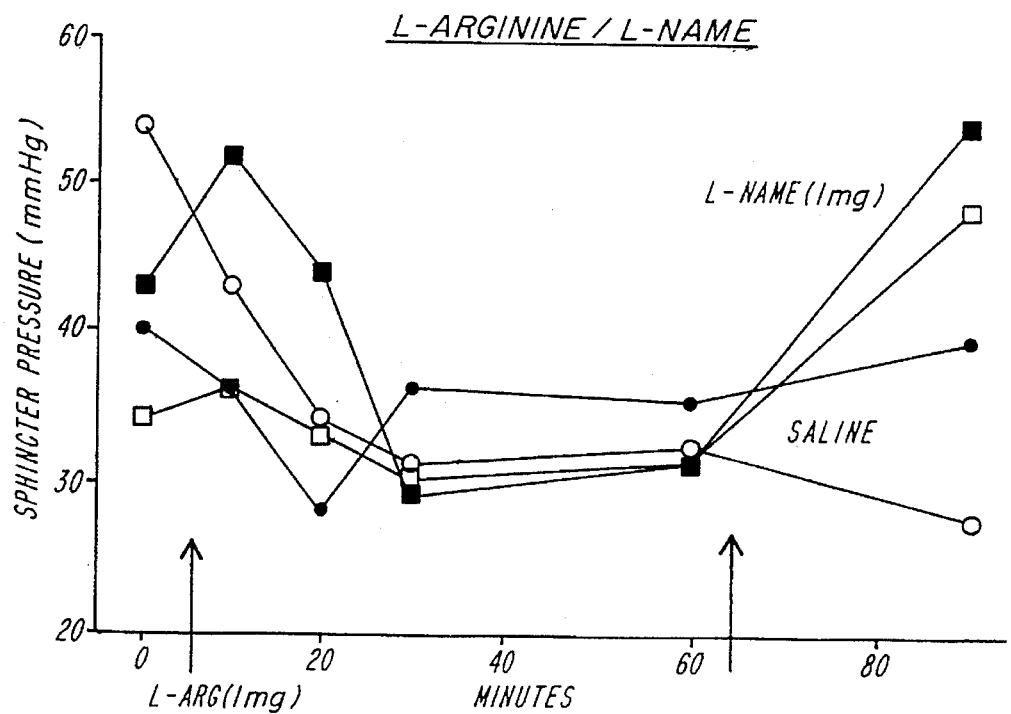
FIG. 2 is a graph of sphincter pressure as a function of time after a combination of L-arginine and $N^G$-nitro-L-arginine methyl ester (L-NAME) is applied.

After 60 minutes, animals treated with 0.01 mg and 1 mg L-arginine per 0.1 ml carrier are further treated with a rectal instillation of 1 mg per 0.1 ml $N^G$-nitro-L-arginine methyl ester (L-NAME). In FIG. 2, each curve represents a different animal subject. L-NAME or saline is introduced into the rectum of each subject just after the 60 min measurement point. As illustrated in FIG. 2, treatment with L-NAME leads to a reversal of the decline in sphincter pressure toward baseline values (Table 1). Treatment with saline, however, does not affect lowered rectal pressure.

TABLE I

| L-Arg (mg/0.1 ml) | n | Baseline | L-ARGININE/L-NAME[1] (1 MG) MINUTES AFTER L-ARG | | | | n | |
|---|---|---|---|---|---|---|---|---|
| | | | 10 | 20 | 30 | 60 | | 90 |
| 0.0001 | 4 | 56.0 ± 2.7 | 55.5 ± 2.1 | 52.0 ± 3.3 | 47.2 ± 1.6 | 49.8 ± 1.9 | 4 | 52 ± 1.0 |
| 0.01 | 6 | 40.7 ± 3.5 | 40.0 ± 3.6 | 33.3 ± 5.4 | 33.3 ± 5.5 | 26.3 ± 3.8* | 3 | 24.7 |
| | | | | | | L-NAME | 3 | 32.7 |
| 1 | 5 | 43.4 ± 3.1 | 40.4 ± 3.2 | 34.0 ± 2.7 | 29.8 ± 2.1 | 32.6 ± 0.8* | 2 | 33 |
| | | | | | | L-NAME | 2 | 51 |

EXAMPLE II

L-Arginine in K-Y Jelly

Figure 3:
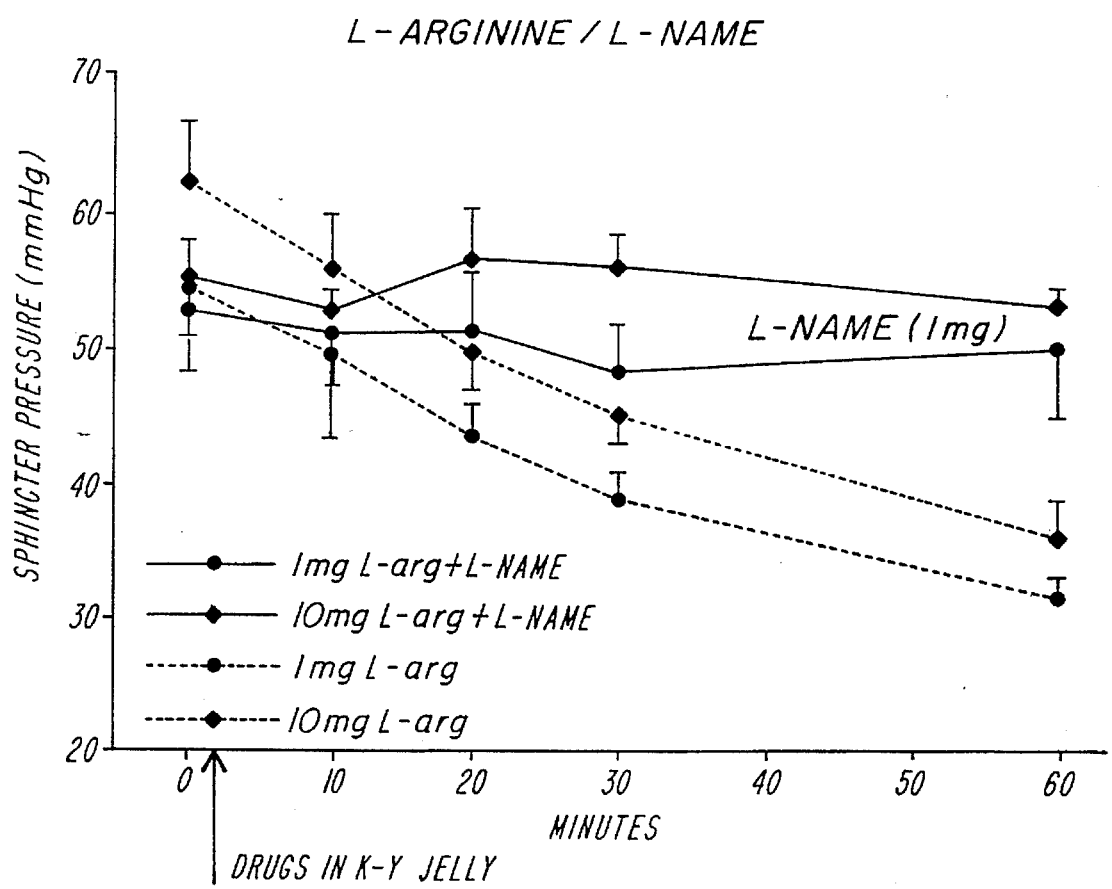
FIG. 3 is a graph of sphincter pressure as a function of time after a combination of L-arginine and $N^G$-nitro-L-arginine methyl ester in K-Y jelly is applied.

L-arginine in doses of 0.0001 mg, 0.01 mg, 1.0 mg and 10 mg per 0.1 ml are mixed in K-Y jelly or a suppository before insertion into the rectum, as described above for testing of L-Arginine in solution. As illustrated in FIG. 3, when mixed with K-Y jelly, L-arginine in a dose of 1 or 10 mg/0.1 ml results in a decline in sphincter pressure ($p<0.05$). This decline in pressure is inhibited if L-NAME (1 mg/0.1 ml) is admixed with the K-Y jelly at the same time (FIG. 3).

USE

The topical preparation of the invention is effective for relieving the pain of hemorrhoids or for treating conditions resulting from spasms of sphincters of the GI tract. The prompt action and extended time of effect of L-arginine provides useful clinical applications of this compound for the treatment of hemorrhoidal pain or conditions associated with sphincter spasm, such as fissure in ano. Due to the similar physiology of the sphincters and muscular walls of the GI tract, the topical preparation of the invention is effective for treating spasms of the sphincters and muscles of the human GI tract in general, including Zenkers diverticulum, achalasia, esophageal spasm (nutcracker esophagus), hypertrophic pyloric stenosis, pancreatitis, irritable bowel disease, Hirshprungs disease (bowel obstruction), and the like. Sphincters and smooth muscles in the esophagus, stomach, and intestine can be treated with L-arginine in an ingestible formula, e.g., an infant formula or a sucker. Precise dosages and frequency requirements will vary with the severity of the particular condition and the individual patient. However, such requirements can easily be determined by the ordinary skilled practitioner and/or methods well known in the art.

A variety of inflammatory ailments are associated with spasm and pain in the anorectal area, such as thrombosed hemorrhoids, fistulae in ano, and the rectal surgery required to treat these conditions. For example, hemorrhoids result from dilation of the veins of the anorectal area, and is often accompanied by bleeding, thrombosis and inflammation. The pain associated with hemorrhoids is due primarily to inflammation adjacent to the anal sphincter. While not bound by any theory, hemorrhoidal pain and related inflammatory conditions can be moderated by relaxing the sphincter muscles. Adults suffering from rectal or hemorrhoidal pain can be treated with approximately 5–10 ml of the topical preparation in similar concentrations as described above. Other diseases requiring painful surgery, such as anal condyloma and local excisions of polyps and tumors can also benefit by prevention of sphincter spasm.

The amino acid L-arginine has not been applied topically to the rectal mucosa of man. However, it has been given to cancer patients by mouth in doses of 25 g per day for 7 days (Shou et al., Ann. Surg. 208:512–523 (1988)) and to healthy volunteers in doses of 30 g per day for 3 days (Brittenden et al., Surgery 115:205–212 (1994)) without adverse effect. In addition, L-arginine in saline has been administered into the jejunum in doses up to 40 mmol/l, and has been given intravenously and by intracoronary infusion at a dose of 50 mg/min. The animals used in these studies were awake during testing and did not exhibit any adverse effects with regard to diarrhea or local rectal irritation. At the conclusion of the study, the animals were normally active, took food and water and had no apparent adverse effects.

Although the invention has been shown and described with respect to illustrative embodiments thereof, it should be appreciated that the foregoing and various other changes, omissions and additions in the form and detail thereof may be made without departing from the spirit and scope of the invention as delineated in the claims.

What is claimed is:

1. A method of treating hemorrhoidal pain or other medical condition arising from a spasm in the smooth muscle of the gastrointestinal tract of a patient, said method comprising:

applying a topical preparation of L-arginine in an pharmaceutically acceptable carrier to an area of the gastrointestinal tract of said patient exhibiting said hemorrhoidal pain or other medical condition in an amount effective to treat said condition.

2. The method of claim 1, wherein said medical condition arises from a spasm in a sphincter of the gastrointestinal tract of said patient, said sphincter of the gastrointestinal tract being selected from the group consisting of internal anal sphincter, lower esophageal sphincter, pyloric sphincter, sphincter of Oddi, and ileocolic sphincter.

3. The method of claim 1, wherein said patient is exhibiting a medical condition selected from the group consisting of hemorrhoidal pain, post-operative rectal pain, anal fissure, anal rectal abcess, rectal sphincter spasm, thrombosed hemorrhoids, Zenkers diverticulum, achalasia, esophageal spasm, hypertrophic pyloric stenosis, pancreatitis, irritable bowel disease, and Hirshprungs disease.

4. The method of claim 1, wherein said pharmaceutically acceptable carrier is water soluble jelly.

5. The method of claim 1, wherein said pharmaceutically acceptable carrier is an anal suppository.

6. The method of claim 1, wherein said pharmaceutically acceptable carrier is an electrolyte solution.

7. The method of claim 1, wherein said pharmaceutically acceptable carrier is a dissolvable sucker.

8. The method of claim 1, wherein the concentration of said L-arginine in said pharmaceutically acceptable carrier is in the range of approximately 0.01 mg to 10 mg per ml.

9. A topical preparation for treating hemorrhoidal pain or other medical condition arising from a spasm in the smooth muscle of the gastrointestinal tract, said preparation comprising:

a therapeutically effective amount of L-arginine; and a pharmaceutically acceptable carrier, said carrier comprising a vehicle for topical administration of said L-arginine to an area of the gastrointestinal tract affected by said medical condition, said pharmaceutically acceptable carrier selected from the group consisting essentially of water soluble jelly, anal suppository, enema solution, dimethylsulfoxide, and dissolvable sucker.

10. The topical preparation of claim 9, wherein the concentration of L-arginine is in the range of approximately 0.01 mg to 10 mg per ml.

11. An article of manufacture comprising packaging material and a pharmaceutical agent contained within said packaging material, wherein said pharmaceutical agent is therapeutically effective for treating hemorrhoidal pain or other medical condition arising from a spasm in the smooth muscle of the gastrointestinal tract of a patient, and wherein the packaging material comprises a label which indicates that the pharmaceutical agent can be used for treating hemorrhoidal pain or other medical condition arising from a spasm in the smooth muscle of the gastrointestinal tract of said patient, and wherein said pharmaceutical agent comprises L-arginine in a pharmaceutically acceptable carrier suitable for topical application.

12. A method of treating rectal sphincter spasm, comprising:

applying a topical preparation of L-arginine in a pharmaceutically acceptable carrier to the rectal sphincter of a patient suffering rectal sphincter spasm in an amount effective to reduce said spasm.

13. The method of claim 12, wherein said pharmaceutically acceptable carrier is water soluble jelly.

14. The method of claim 12, wherein said pharmaceutically acceptable carrier is a enema solution.

15. The method of claim 12, wherein said pharmaceutically acceptable carrier is an anal suppository.

16. The method of claim 12, wherein the concentration of said L-arginine in said pharmaceutically acceptable carrier is in the range of approximately 0.001 mg to 10 mg per ml.

17. A method of treating pain in the anorectal area, comprising:

providing a patient suffering pain in the anorectal area;

applying a topical preparation of L-arginine in a pharmaceutically acceptable carrier to the site of said pain in said anorectal area of said patient in an amount effective to reduce said pain.

18. The method of claim 17, wherein said pharmaceutically acceptable carrier is water soluble jelly.

19. The method of claim 17, wherein said pharmaceutically acceptable carrier is an anal suppository.

20. The method of claim 17, wherein the concentration of said L-arginine in said pharmaceutically acceptable carrier is in the range of approximately 0.001 mg to 10 mg per ml.

21. The method of claim 17, wherein said pain in the anorectal area is hemorrhoidal pain.

22. The method of claim 17, wherein said pain in the anorectal area is post-operative rectal pain.

23. The article of manufacture of claim 11, wherein said medical condition arises from a spasm in a sphincter of the gastrointestinal tract of said patient, said sphincter of the gastrointestinal tract being selected from the group consisting of internal anal sphincter, lower esophageal sphincter, pyloric sphincter, sphincter of Oddi, and ileocolic sphincter.

24. The article of manufacture of claim 11, wherein said medical condition is selected from the group consisting of hemorrhoidal pain, post-operative rectal pain, anal fissure, anal rectal abcess, rectal sphincter spasm, thrombosed hemorrhoids, Zenkers diverticulum, achalasia, esophageal spasm, hypertrophic pyloric stenosis, pancreatitis, irritable bowel disease, and Hirshprungs disease.

25. The article of manufacture of claim 11, wherein said pharmaceutically acceptable carrier is water soluble jelly.

26. The article of manufacture of claim 11, wherein said pharmaceutically acceptable carrier is an anal suppository.

27. The article of manufacture of claim 11, wherein said pharmaceutically acceptable carrier is an electrolyte solution.

28. The article of manufacture of claim 11, wherein said pharmaceutically acceptable carrier is a dissolvable sucker.

29. The article of manufacture of claim 11, wherein the concentration of said L-arginine in said pharmaceutically acceptable carrier is in the range of approximately 0.01 mg to 10 mg per ml.

* * * * *